US00H002211H

(19) United States

(12) Statutory Invention Registration

Pavri et al.

(10) Reg. No.: US H2211 H

(43) Published: Mar. 4, 2008

(54) STABILIZATION OF FLUORINATED KETONES

(75) Inventors: Neville Pavri, Evans, GA (US); Danny Graham, Martinez, GA (US); Mark Harris, N. Augusta, SC (US); Paul Mazzell, Aiken, SC (US)

(73) Assignee: Halocarbon Products Corporation, River Edge, NJ (US)

(21) Appl. No.: 11/687,774

(22) Filed: Mar. 19, 2007

(51) Int. Cl.
*C07C 45/86* (2006.01)

(52) U.S. Cl. ..... 568/304

(58) Field of Classification Search ..... None
See application file for complete search history.

*Primary Examiner*—Michael J. Carone

(74) *Attorney, Agent, or Firm*—Kurt G. Briscoe; Norris McLaughlin & Marcus, P.A.

(57) ABSTRACT

Fluorinated ketones, for example, 1,1,1-trifluoroacetone, can be stabilized against storage degradation by combining with a content of hexafluoroisopropanol (HFIP). Containers containing the stabilized mixture show prolonged storage times compared to containers containing the fluorinated ketones alone. The stabilized mixture can be used as a starting material for reactions requiring fluorinated ketones, for example, 1,1,1-trifluoroacetone, as a starting material.

14 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

STABILIZATION OF FLUORINATED KETONES

BACKGROUND OF THE INVENTION

1. Field of the Invention

The present invention relates generally to fluorinated ketones.

2. Description of Related Art

Fluorinated ketones are useful intermediates in the synthesis of pharmaceutical products. Fluorinated ketones have been found to degrade upon storage and cannot be used after they have been stored for extended periods without sacrificing yield in subsequent transformations; this causes the process to be economically unfavorable. Of particular interest is 1,1,1-trifluoroacetone, which has been used as an important intermediate for the preparation of biologically active compounds (for example, J. Med. Chem. 1975 (18), 895, J. Med. Chem. 1983 (26), 950 and Bull. Soc. Chim. France 1986, 933).

We have found that 1,1,1-trifluoroacetone is stable if stored in glass containers. However, the low boiling point (21°–22° C.) of 1,1,1-trifluoroacetone makes this problematic on a large scale. Also, shipping a low boiling liquid in glass would not be the most desirable method of shipping such a material. Upon storage in metal containers for a prolonged period of time, 1,1,1-trifluoroacetone shows a substantial amount of degradation. It is known in the prior art that 1,1,1-trifluoroacetone can be stabilized by acids having a pKa of 4 or below (U.S. Pat. No. 6,531,075). The amount of acid that is added plays a critical role, since the presence of excess acid can promote the degradation of trifluoroacetone.

Accordingly, there remains a need in the art to discover other materials that can be used to stabilize fluorinated ketones in general, and 1,1,1-trifluoroacetone in particular.

BRIEF SUMMARY OF THE INVENTION

This and other objectives were met with the present invention, which provides in a first embodiment for a composition stabilized against degradation during storage, wherein the composition comprises (a) a content of a fluorinated ketone and (b) a content of hexafluoroisopropanol (HFIP) that is effective to stabilize the content of fluorinated ketone against degradation during storage.

The present invention relates in a second embodiment to a container containing a content of the inventive composition.

The present invention relates in a third embodiment to a method of stabilizing a content of a fluorinated ketone against degradation by combining the content of fluorinated ketone with a content of HFIP that is effective to stabilize the content of fluorinated ketone against degradation during storage.

DETAILED DESCRIPTION OF THE INVENTION

The fluorinated ketones that can be protected by the present invention include, in principal, any such fluorinated ketone. In one preferred embodiment, the fluorinated ketone is 1,1,1-trifluoroacetone.

In order to stabilize the fluorinated ketone against degradation during storage, the content of the fluorinated ketone is combined with a content of HFIP that is effective to stabilize the fluorinated ketone against degradation during storage. In a preferred embodiment, the content of fluorinated ketone in a composition comprising both the fluorinated ketone and the HFIP ranges from about 80% to about 99.99% by weight; and the amount of HFIP in the composition ranges from about 0.01% to about 20% by weight. In a very preferred embodiment, the amount of HFIP in the composition ranges from about 0.4% to about 15% by weight. In an especially preferred embodiment, the amount of HFIP in the composition ranges from about 0.5% to about 6% by weight.

When the storage stabilized composition of the present invention is placed into a storage container, the fluorinated ketone content contained therein exhibits a prolonged stabilization against degradation than a content of the fluorinated ketone alone. The type of container is not believed to be critical, and any suitable container can be used, for example, glass, metal or plastic. In a preferred embodiment, the container is metal, particularly, carbon steel or a stainless steel container, especially 316SS.

The invention will now be described in greater detail with reference to the following non-limiting examples.

EXAMPLES

Experiment 1

50 mL of 99.75% pure (based on GC assay) 1,1,1-trifluoroacetone were added to a carbon steel container (#1).

50 mL of 99.75% pure (based on GC assay) 1,1,1-trifluoroacetone and 50 ppm of HCl by weight were added to a carbon steel container (#2).

50 mL of material that was 93.56% 1,1,1-trifluoroacetone, 0.7% unknown and 5.67% HFIP were added to a carbon steel container (#3).

50 mL of 99.75% pure (based on GC assay) 1,1,1-trifluoroacetone and 0.5% HFIP by weight were added to a carbon steel container (#4).

The containers were added to a 54° C. oven and maintained at that temperature for 2 weeks and then analyzed by GC.

| Container | % HFIP | % Trifluoroacetone | % Degradation |
|---|---|---|---|
| #1 | <0.001 | 69.76 | 28.4 |
| #2 | <0.001 | 87.56 | 11.94 |
| #3 | 5.97 | 88.04 | 5.01 |
| #4 | 0.5 | 89.60 | 10.40 |

Based on the results shown in the above table it was apparent that HFIP added to 1,1,1-trifluoroacetone stabilized the ketone. Better results were obtained using approximately 5 wt % of HFIP compared to 0.5 wt % HFIP or 50 ppm of strong acid under these accelerated test conditions.

We then decided to see if the type of steel used would make a difference. The following experiment was carried out.

Experiment 2

1,1,1-trifluoroacetone was spiked with approximately 14% HFIP and added to a carbon steel container and a stainless steel (316SS) container. The material was stored in these containers at ambient temperature for 4 months and analyzed by GC.

| Container | % HFIP | % Degradation |
|---|---|---|
| Carbon steel | 14.95 | 0.71 |
| 316 SS | 13.79 | 0.01 |

Based on the above results it would appear that 316 SS is a preferred material of construction for containers used in the storage of stabilized 1,1,1-trifluoroacetone. Next, we attempted to find a preferred amount of HFIP needed to stabilize 1,1,1- trifluoroacetone in a 316 SS container. The results are shown below.

Experiment 3

| Container | % HFIP w/w | % Degradation |
|---|---|---|
| 316 SS | 500 ppm | 1.2% |
| 316 SS | 5% | 0.1% |
| 316 SS | 15% | 0.1% |

Summarizing the foregoing, we have discovered that hexafluoroisopropanol can be used to stabilize 1,1,1-trifluoroacetone and other fluorinated ketones in storage containers, especially if stored in stainless steel containers. The use of HFIP to stabilize the fluorinated ketone is an improvement over the prior art which used a strong acid to achieve the same result. Since excess strong acid can itself cause degradation of 1,1,1- trifluoroacetone and other fluorinated ketones, the use of hexafluoroisopropanol overcomes this drawback. It may be possible to accomplish many chemical transformations of 1,1,1-trifluoroacetone using the trifluoroacetone/hexafluoroisopropanol mixture as such. If for some reason the presence of hexafluoroisopropanol causes a problem in the chemical transformation, the trifluoroacetone can be easily separated from HFIP (b.p. 57° C.) just prior to use by distillation, especially fractional distillation.

It should be understood that the preceding is merely a detailed description of one preferred embodiment or of a small number of preferred embodiments of the present invention and that numerous changes to the disclosed embodiment(s) can be made in accordance with the disclosure herein without departing from the spirit or scope of the invention. The preceding description, therefore, is not meant to limit the scope of the invention in any respect. Rather, the scope of the invention is to be determined only by the appended issued claims and their equivalents.

What is claimed is:

1. A composition stabilized against degradation during storage, said composition comprising (a) a content of a fluorinated ketone and (b) a content of hexafluoroisopropanol (HFIP) that is effective to stabilize said content of fluorinated ketone against degradation during storage.

2. The composition according to claim 1, wherein the fluorinated ketone is 1,1,1-trifluoroacetone.

3. The composition according to claim 1, wherein the content of fluorinated ketone in said composition ranges from about 80% to about 99.99% by weight; and the amount of HFIP in said composition ranges from about 0.01% to about 20% by weight.

4. The composition according to claim 3, wherein the amount of HFIP in said composition ranges from about 0.4% to about 15% by weight.

5. The composition according to claim 4, wherein the amount of HFIP in said composition ranges from about 0.5% to about 6% by weight.

6. A container containing a content of a composition according to any one of claims 1–5.

7. The container according to claim 6, which is metal.

8. A method of stabilizing a content of a fluorinated ketone against degradation, said method comprising combining said content of said fluorinated ketone with a content of HFIP that is effective to stabilize said content of fluorinated ketone against degradation during storage.

9. The method according to claim 8, wherein the fluorinated ketone is 1,1,1-trifluoroacetone.

10. The method according to claim 8, wherein the content of fluorinated ketone ranges from about 80% to about 99.99% by weight of a composition comprising both the fluorinated ketone and the HFIP; and the amount of HFIP in said composition ranges from about 0.01% to about 20% by weight.

11. The method according to claim 10, wherein the amount of HFIP in said composition ranges from about 0.4% to about 15% by weight.

12. The method according to claim 11, wherein the amount of HFIP in said composition ranges from about 0.5% to about 6% by weight.

13. A process comprising reacting a fluorinated ketone with at least one other chemical, wherein the fluorinated ketone is provided to said reacting in the form of a composition according to claim 1.

14. The process according to claim 13, wherein the fluorinated ketone is 1,1,1-trifluoroacetone.

* * * * *